US011324469B2

(12) United States Patent
Jacobs et al.

(10) Patent No.: US 11,324,469 B2
(45) Date of Patent: May 10, 2022

(54) INFORMATICS RADIOMICS INTEGRATION SYSTEM (IRIS): A NOVEL COMBINED INFORMATICS AND RADIOMICS METHOD FOR INTEGRATION OF MANY TYPES OF DATA FOR CLASSIFICATION INTO DIFFERENT GROUPS FOR IMPROVED VISUALIZATION

(71) Applicant: THE JOHNS HOPKINS UNIVERSITY, Baltimore, MD (US)

(72) Inventors: Michael A. Jacobs, Sparks, MD (US); Vishwa S. Parekh, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 472 days.

(21) Appl. No.: 15/334,407

(22) Filed: Oct. 26, 2016

(65) Prior Publication Data
US 2017/0112459 A1 Apr. 27, 2017

Related U.S. Application Data

(60) Provisional application No. 62/246,230, filed on Oct. 26, 2015.

(51) Int. Cl.
| | |
|---|---|
| *G01N 33/48* | (2006.01) |
| *A61B 6/00* | (2006.01) |
| *A61B 5/055* | (2006.01) |
| *G06T 7/00* | (2017.01) |
| *G06K 9/62* | (2022.01) |
| *G16H 30/20* | (2018.01) |
| *A61B 6/03* | (2006.01) |

(52) U.S. Cl.
CPC ............ *A61B 6/5217* (2013.01); *A61B 5/055* (2013.01); *G06K 9/6219* (2013.01); *G06K 9/6251* (2013.01); *G06K 9/6253* (2013.01); *G06T 7/0012* (2013.01); *G16H 30/20* (2018.01); *A61B 6/037* (2013.01); *G06T 2207/10088* (2013.01); *G06T 2207/10104* (2013.01); *G06T 2207/30068* (2013.01); *G06T 2207/30096* (2013.01)

(58) Field of Classification Search
None
See application file for complete search history.

(56) References Cited

U.S. PATENT DOCUMENTS

| | | | | |
|---|---|---|---|---|
| 2010/0016706 | A1* | 1/2010 | Wohlgemuth | A61B 5/055 600/410 |
| 2010/0329529 | A1* | 12/2010 | Feldman | G06K 9/4619 382/131 |
| 2015/0376713 | A1* | 12/2015 | Cress | C12Q 1/6886 514/789 |
| 2016/0242690 | A1* | 8/2016 | Principe | A61B 5/742 |

OTHER PUBLICATIONS

Van Eijk, Ronald, et al. "Visualization of regional gene expression biases by microarray data sorting." BioTechniques 36.4 (2004): 592-596.*
Zhao, Shilin, et al. "Advanced Heat Map and Clustering Analysis Using Heatmap3." (2014). pp. 1-6.*
AUman et al. "Heat Map Visualization of High-Density Clinical Chemistry Data," (Physiol Genomics vol. 31 (2007) pp. 352-356).*
Anand, Anushka. Visual Pattern Detection in High-dimensional Spaces. Diss. University of Illinois at Chicago, 2012.*
Akhbardeh, Alireza, and Michael A. Jacobs. "Comparative analysis of nonlinear dimensionality reduction techniques for breast MRI segmentation." Medical physics 39.4 (2012): 2275-2289.*
Akata, Zeynep, et al. "Label-embedding for image classification." IEEE transactions on pattern analysis and machine intelligence 38.7 (2015): 1425-1438.*
Gong, Yunchao, et al. "A multi-view embedding space for modeling internet images, tags, and their semantics." International journal of computer vision 106.2 (2014): 210-233.*
Mumtaz, Shahzad. Visualisation of bioinformatics datasets. Diss. Aston University, 2015.*
Jacobs, Michael A., et al. "Integrated Multiparametric Radiomics and Informatics System for Characterizing Breast Tumor Characteristics with the OncotypeDX Gene Assay." Cancers 12.10 (2020): 2772.*

(Continued)

*Primary Examiner* — Anna Skibinsky
(74) *Attorney, Agent, or Firm* — Johns Hopkins Technology Ventures (57) ABSTRACT

An embodiment in accordance with the present invention includes a novel informatics method for the integration of different variables or ontologies using an advanced unsupervised machine learning method which will be used to visualize factors not visible to the human observer. These factors can be unknown characteristics between imaging datasets and other factors which will provide insights into the structure of the data. This invention is called the Informatics Radiomics Integration System (IRIS), For example, using clinical data and radiological images, the present invention can determine the relationship between, the structure, clinical variables, histological variables and "distance or relationship" between each input parameter. This integration of information can be used to determine the association between the variables and the relationship to each other for improved diagnosis or for treatment response.

18 Claims, 7 Drawing Sheets

(56) References Cited

OTHER PUBLICATIONS

Kaur, Mandhir, and Rinkesh Mittal. "An efficient scheme for brain tumor detection of MRI brain images using Euclidean distance with FVT." journal of emerging technologies in web intelligence 6 (2014).*

Jacobs, Michael A., et al. "Unsupervised segmentation of multiparameter MRI in experimental cerebral ischemia with comparison to T2, diffusion, and ADC MRI parameters and histopathological validation." Journal of Magnetic Resonance Imaging 11.4 (2000): 425-437.*

* cited by examiner

INFORMATICS RADIOMICS INTEGRATION SYSTEM (IRIS): A NOVEL COMBINED INFORMATICS AND RADIOMICS METHOD FOR INTEGRATION OF MANY TYPES OF DATA FOR CLASSIFICATION INTO DIFFERENT GROUPS FOR IMPROVED VISUALIZATION

CROSS REFERENCE TO RELATED APPLICATION

This application claims the benefit of U.S. Provisional Patent Application No. 62/246,230 filed on Oct. 26, 2015, which is incorporated by reference, herein, in its entirety.

FIELD OF THE INVENTION

The present invention relates generally to medical imaging. More particularly, the present invention relates to a method for integration of many types of data for classification into different groups for improved visualization.

BACKGROUND OF THE INVENTION

When viewing data from various sources, it can be difficult for the average observer to integrate all of the different data sources without additional assistance. In addition, the data sets include information that is not readily visible to the human observer. Visualization of the integrated data must also be provided in a way that is easily understood by the observer. In this way the integrated data can be conveyed to the observer in a limited number of visualizations. Currently, no such system of data integration and simplified visualization exists.

Accordingly, there is a need in the art for a new method for the integration of different variables or ontologies using an advanced unsupervised machine learning method which will be used to visualize factors not visible to the human observer.

SUMMARY OF THE INVENTION

The foregoing needs are met, to a great extent, by the present invention which provides a method of integrating datasets and other factors including receiving input in the form of the datasets and other factors. The method includes mapping the datasets and other factors to a point in a space using a distance metric or correlation coefficient. The method also includes mapping the datasets or other factors to an embedded space. Complex interactions from input sources or domains are detected. Quantitative information is outputted via pairwise correlation of points in the embedded space that are representative of a group of points and a heatmap representative of the correlation of the points is generated.

In accordance with an aspect of the present invention, the method includes space taking the form of a two-dimensional space or a three-dimensional space. The method further includes correlating taking the form of distance. The method can be applied for making medical diagnosis, such as assessing cancer. Embedded space can take the form of a unified description capturing both appearance and dynamics of input processes. The method also includes using a non-transitory computer readable medium.

In accordance with another aspect of the present invention, a system for integrating datasets and other factors includes a source of datasets and other factors. The system also includes a non-transitory computer readable medium programmed for receiving input in the form of the datasets and other factors. The non-transitory computer readable medium is also programmed for mapping the datasets and other factors to a point in a space using a distance metric or correlation coefficient and mapping the datasets or other factors to an embedded space. The system is configured for detecting complex interactions from input sources or domains. Additionally, the system is configured for outputting quantitative information via pairwise correlation of points in the embedded space that are representative of a group of points and generating a heatmap representative of the correlation of the points.

In accordance with yet another aspect of the present invention, the space takes the form of a two-dimensional space or a three-dimensional space. Correlating can take the form of distance. The system can be used for making medical decisions and assessing cancers. Embedded space takes the form of a unified description capturing both appearance and dynamics of input processes. The system can include a computing device. Datasets can be received from an imaging machine. The heatmap can also be outputted to a graphical user interface.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention includes a novel informatics method for the integration of different variables or ontologies using an advanced unsupervised machine learning method which will be used to visualize factors not visible to the human observer. These factors can be unknown characteristics between imaging datasets and other factors which will provide insights into the structure of the data. This invention is called the Informatics Radiomics Integration System (IRIS), For example, using clinical data and radiological images, the present invention can determine the relationship between, the structure, clinical variables, histological variables and "distance or relationship" between each input parameter. This integration of information can be used to determine the association between the variables and the relationship to each other for improved diagnosis or for treatment response.

The present invention uses a system that maps each data set to a point in a 2-D or 3-D space using either a distance metric or correlation coefficient. The data set is further mapped into an embedded space that allows for the detection of complex interactions from different input sources and/or domains (eg. radiological images, clinical variables, and histological information). The embedded space is a unified description capturing both the appearance and dynamics of input processes. Quantitative information is outputted via pair-wise distance (or correlation) of points in the embedded space that are representative of their group. The method creates a new visualization of the data by producing a novel heat map or complex interaction map on any type of ontologies (i.e. images or digital data) to determine the relationships and patterns which enable accurate detection and contribution of each data parameter to the dimension space. Examples of the forms of visualization of the data correlations are provided herein. The system is referred to as Informatics Radiomics Integration System (IRIS).

IRIS is a new machine learning informatics model for detecting complex interactions from different input sources and/or domains (e.g. for patients: radiological images, clinical variables or tests, and histological information or for other data: packet information, visual objects, etc). The IRIS creates a relationship that maps each data set to a point in a 2-D space The IRIS also creates a relationship that maps each data set to a point in a 3-D space. In some embodiments IRIS uses a distance metric (Euclidean or geodesic) into an embedded space. In other embodiments IRIS uses a correlation coefficient (Jaccard measure or something similar) into an embedded space.

The informatics embedded space is a unified description capturing both the appearance and dynamics of the input processes. Pair-wise distance (or correlation) of points in the embedded space represents their group. The present method of applying IRIS on data will produce a novel heatmap on any type of ontologies (i.e. images or digital data). The present method of applying IRIS on data will also produce a novel complex interaction map on any type of ontologies (i.e., images or digital data). IRIS determines the interrelationships and patterns that enable accurate detection and contribution of each data parameter to the dimensional space.

IRIS provides fast implementation of advanced unsupervised machine learning combined with statistical methods real-time applications. The use of the novel IRIS detects complex interactions from different input sources or domains (e.g. radiological images, clinical variables, and histological information). The embedded space is a unified description capturing both the appearance and dynamics of input processes. Quantitative information is outputted via pair-wise distance (or correlation) of points in the embedded space represents their group. The method creates a visualization of the data by producing a novel heat map or complex interaction map on any type of ontologies (i.e. images or digital data) to determine the relationships and patterns which enable accurate detection and contribution of each data parameter to the dimension space.

According to an embodiment of the present invention, a computing device includes a non-transitory computer readable medium programmed to execute the method. Data to be processed by the non-transitory computer readable medium is received. The data can be from a source external to the computing device and non-transitory computer readable medium or the source can be from the computing device, a networked device, or any other source known to or conceivable to one of skill in the art. Sources can include, but are not limited to, imaging devices, a networked or remote server, data input by a user, or any other source of data known to or conceivable by one of skill in the art. Other factors to be considered by the non-transitory computer readable medium can also be received in this way.

After the data to be processed is received, the non-transitory computer readable medium is used to process the data sets and other factors. The data sets and other factors are mapped to a point in space using a distance metric or correlation coefficient. The data sets and other factors are also mapped to an embedded space. Complex interactions are detected from input sources or domains. Quantitative information is outputted via pairwise correlation of points in the embedded space that are representative of a group of points, and a heatmap representative of the correlation of the points is also generated. These outputs can be visualized by the user via a GUI or other device known to one of skill in the art. The outputs can be interactive and manipulatable by a user.

Figure 1:
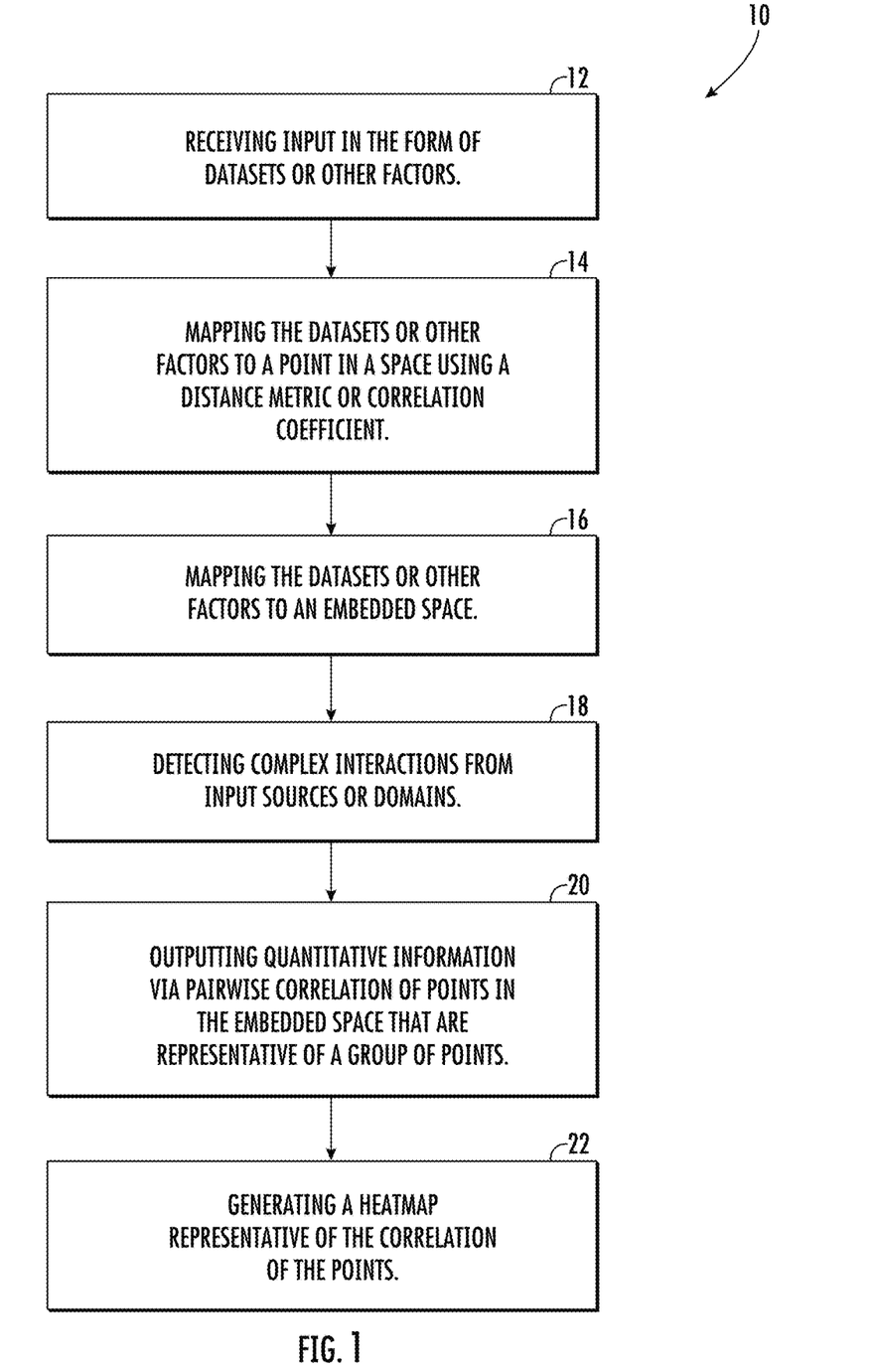
FIG. 1 illustrates a flow diagram illustrating the execution of the steps of the method, according to an embodiment of the present invention.

FIG. 1 illustrates a flow diagram 10 illustrating the execution of the steps of the method. In step 12, data is received from the data source. In step 14, the data sets and other factors are mapped to a point in space using a distance metric or correlation coefficient. The data sets and other factors are also mapped to an embedded space, in step 16. Complex interactions are detected from input sources or domains, in step 18. In step 20, quantitative information is outputted via pairwise correlation of points in the embedded space that are representative of a group of points, and, in step 22, a heatmap representative of the correlation of the points is also generated.

EXAMPLES

Figure 2:
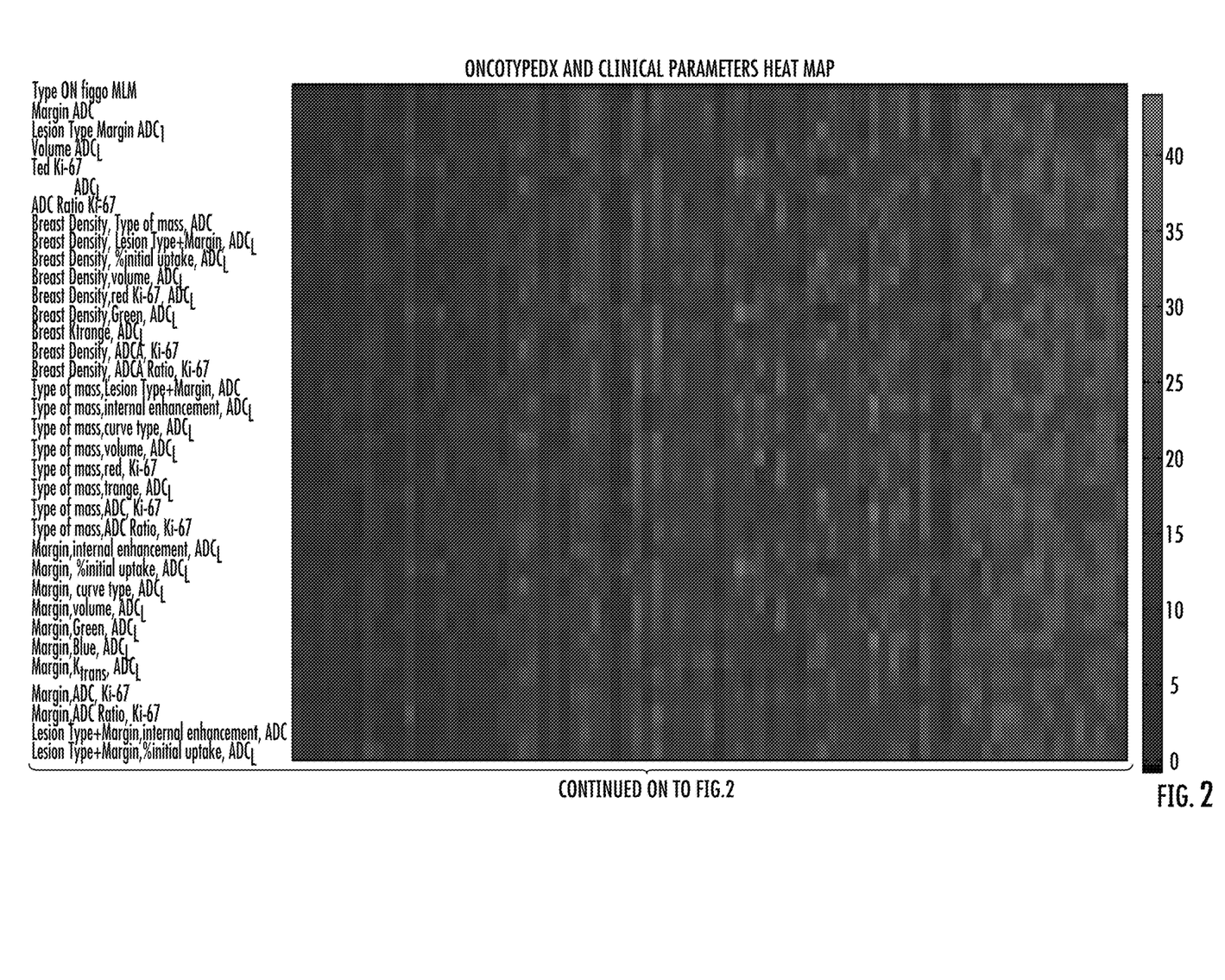
FIG. 2 illustrates a graphical view of a heat map showing correlation between clinical and radiological parameters and risk, according to an embodiment of the present invention.
Figure 3:
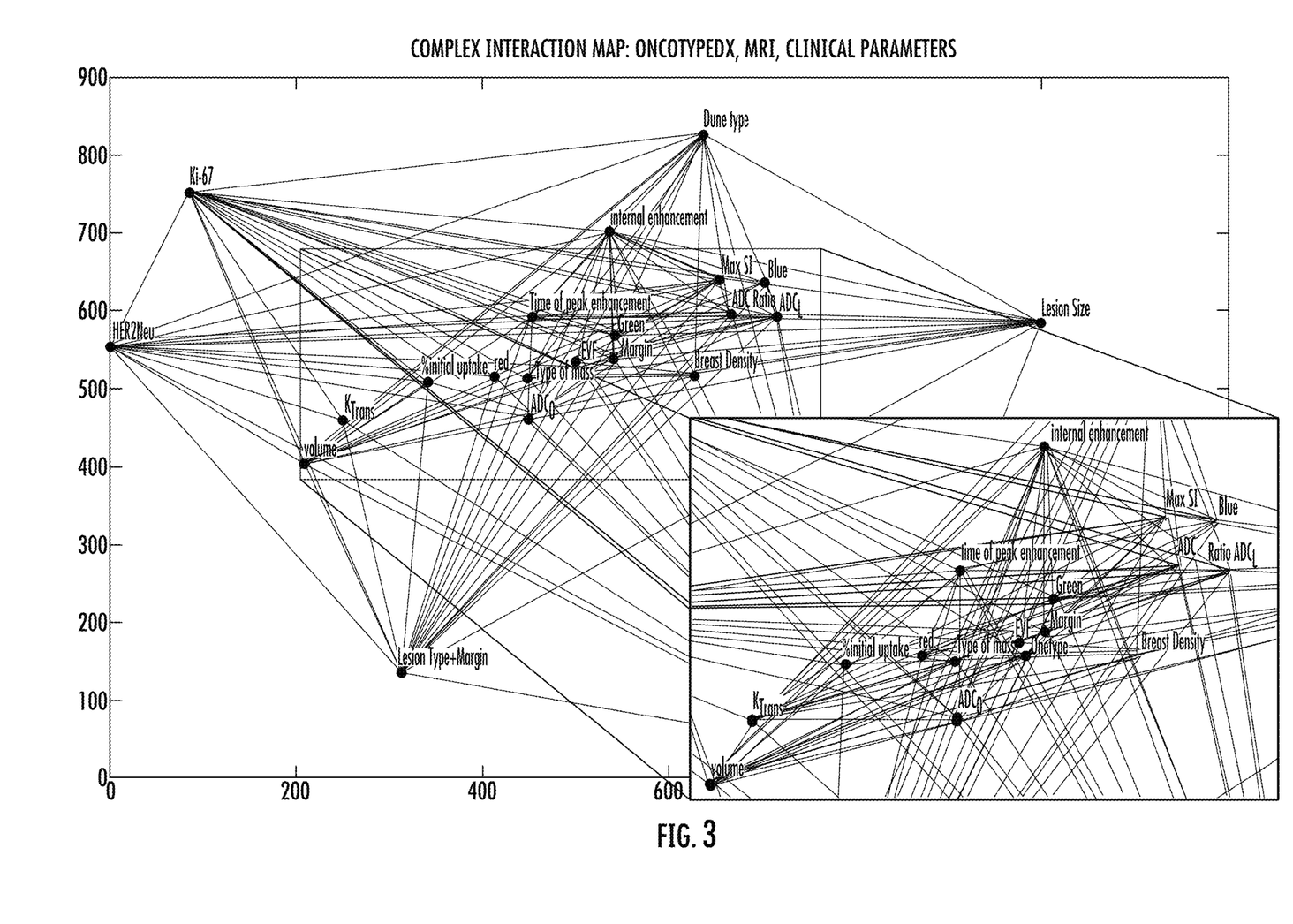
FIG. 3 illustrates a graphical view of the complex interaction mapping provides visualization of the radiological and clinical parameters with the OncotypeDX score, according to an embodiment of the present invention.

The following examples are included to further illustrate the invention. These examples are not meant to be considered limiting. In one exemplary radiographic application, emerging data on breast cancer suggest that different breast cancer subtypes (phenotypes) may respond differently to available adjuvant therapies. FIG. 2 illustrates a graphical view of a heat map showing correlation between clinical and radiological parameters and risk. The informatics heat map demonstrates the stratification of the radiological parameters correlated with the OncotypeDX score. There is a growing understanding that not all patients benefit equally from systemic therapies, and therapeutic approaches are being increasingly personalized based on predictive biomarkers of clinical benefit. Optimal use of established and novel imaging methods, such as magnetic resonance imaging (MRI) and positron emission tomography (PET), can simultaneously identify key functional parameters and provide unique multiparametric imaging phenotypes of breast cancer. Therefore, IRIS provides a new informatics tool that integrates clinical variables, derived from imaging and clinical workup, to compare with the 21-gene array assay, OncotypeDX. The OncotypeDX stratifies patient into three risk groups: low, medium, and high risk. In particular, IRIS compares the traditional clinical parameters and advanced MRI parameters with the molecular expression rate defined by the OncotypeDX. FIG. 3 illustrates a graphical view of the complex interaction mapping provides visualization of the radiological and clinical parameters with the OncotypeDX score.

Figure 4:
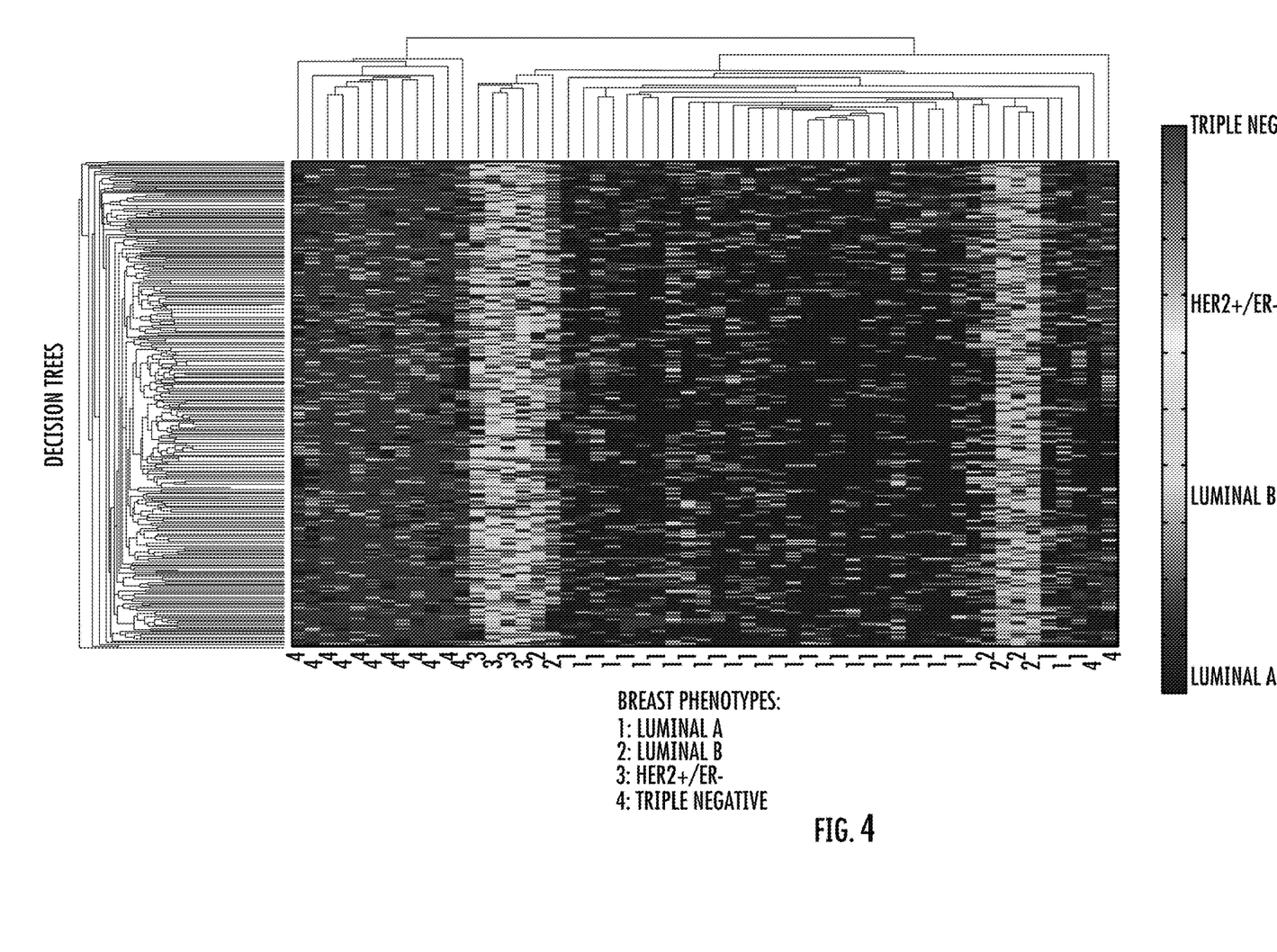
FIG. 4 illustrates a graphical view of the IRIS mapping visualization of the PET and MRI radiological and clinical parameters for the classification of the histological breast phenotype, according to an embodiment of the present invention.

Extending this model to include more advanced imaging methods, the present invention discerns the relationships between the imaging parameters and different breast cancer subtypes (phenotypes). In particular, using magnetic resonance imaging (MRI) and positron emission tomography (PET). This separation of the different subtypes will allow for a "virtual biopsy" of cancer tissue. This "virtual biopsy" of the tissue will identify key functional imaging parameters of phenotypes in breast cancer. FIG. 4 illustrates a graphical view of the IRIS mapping visualization of the PET and MRI radiological and clinical parameters for the classification of the histological breast phenotype. As shown in FIG. 4, the virtual biopsy is derived from imaging and clinical workup and compared to the histological subtype, demonstrating the power of the IRIS system to discern different phenotypes of breast cancer.

Figure 5:
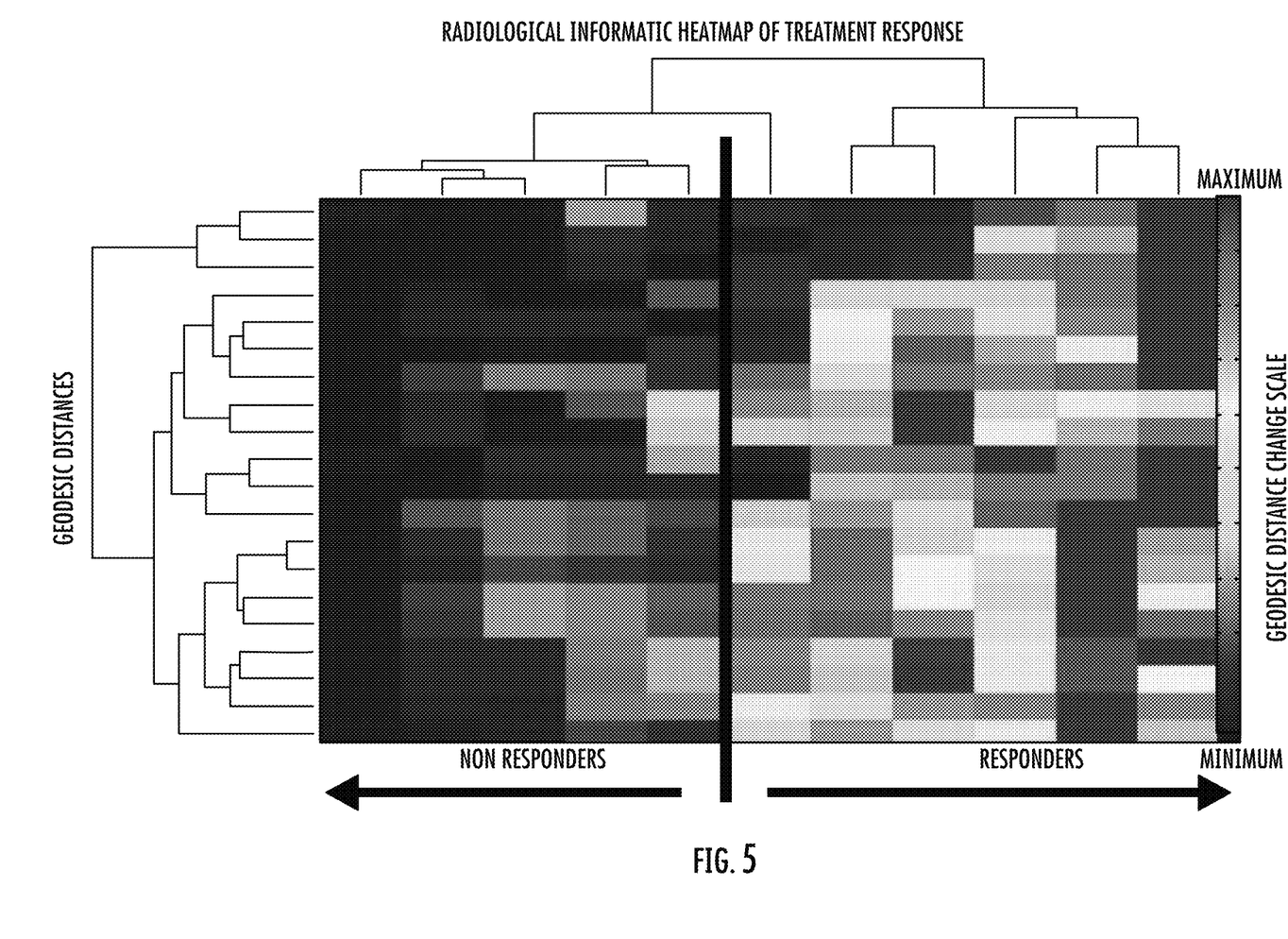
FIG. 5 illustrates a graphical view of a heatmap for treatment response, according to an embodiment of the present invention.

Different biomarkers can be used to predict treatment response in patients. However, the ability to integrate these data is sometimes very challenging. The drive towards "personalized based" medicine is increasing and due to the understanding that not all patients benefit equally from systemic therapies, and other therapeutic approaches. Therefore, a method that can provide predictive markers is needed. FIG. 5 illustrates a graphical view of a heatmap for treatment response. As shown in FIG. 5, the IRIS is able to separate responders from non-responders after the first cycle of treatment in a set of breast cancer patients undergoing treatment. This could have major implications in oncology, since the FDA recently announced a fast track approval for different treatments, if accurate response metrics can be developed and be predictive. This predictive power could spare the patient enormous costs both physically and economically. FIG. 4 illustrates the IRIS mapping visualization of the treatment response metric in breast cancer patients undergoing primary systemic treatments.

The present invention can be applied to a number of areas, detailed below. These applications are merely examples and are not meant to be considered limiting. One exemplary application includes combining different high dimensional data (visual, binary, etc) to visualize factors not visible to the human observer such as unknown characteristics between imaging datasets and other factors. IRIS has the ability to detect the interrelationships of the different ontologies (objects) using the distance or structure of each ontology. IRIS could be used to predict outcomes from very different input variables. IRIS provides new visualization methods for easier interpretation of data. Diagnosis can be provided from combined clinical and radiological variables. The present invention can be used for treatment Response after treatment using combined clinical and radiological variables. Object (Imaging and other medical data) location and monitoring can also be done. Health monitoring can be provided by combining all electronic medical data for patient subjects. The present invention can detect outliers for information services or intrusion detection using the complex interactions of information packets over networks. IRIS can provide Computer Aided Visualization of relationships of different input data, Computer Aided Diagnosis Software for Diagnosis, and Computer Aided Treatment response. The present invention can be used as a predication system for big data informatics analysis. Additionally, the present invention can be used for the integration of different ontologies into a relevant embedded imaging for rapid interpretation of the different relationships of data.

The steps and analysis of the present invention can be carried out using a computer, non-transitory computer readable medium, or alternately a computing device or non-transitory computer readable medium incorporated into the imaging device. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. The computing device can also take the form of an operating console computer for the imaging device. The operating console is a non-generic computer specifically designed by the scanner manufacturer for bilateral (input output) communication with the scanner. It is not a standard business or personal computer that can be purchased at a local store. Additionally this console computer carries out communications with the scanner through the execution of proprietary custom built software that is designed and written by the scanner manufacturer for the computer hardware to specifically operate the scanner hardware.

The many features and advantages of the invention are apparent from the detailed specification, and thus, it is intended by the appended claims to cover all such features and advantages of the invention, which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of integrating datasets and other factors comprising:
   receiving clinical data input with a processor in the form of the datasets and other factors, wherein the datasets and other factors are from various input sources, and wherein the datasets include computer-based medical image data, such as from magnetic resonance imaging or positron emission tomography;

mapping, using the processor, each of a number of input parameters to a point in an informatics embedded space using a machine learning informatics model in combination with a distance metric or correlation coefficient to provide a unified description to capture both appearance and dynamics of the input, wherein the clinical data input is a number of input parameters;

detecting complex interactions between the points within the informatics embedded space, using the processor, wherein the processor implements advanced unsupervised machine learning combined with statistical methods to detect the complex interactions;

outputting quantitative information with a pairwise correlation of points in the informatics embedded space that are representative of a group of points, using the processor;

generating a heatmap representative of the correlation of the points to determine relationships and patterns to enable detection and contribution of each data parameter to the embedded space, using the processor;

outputting the heatmap to a user as a visualization, using the processor and a graphical user interface, wherein the heatmap is usable for diagnosis and treatment response.

2. The method of claim 1 further comprising the space taking the form of a two-dimensional space.

3. The method of claim 1 further comprising the space taking the form of a three-dimensional space.

4. The method of claim 1 further comprising applying the method to making medical diagnosis.

5. The method of claim 4 further comprising assessing cancer.

6. The method of claim 1 further comprising embedded space taking the form of a unified description capturing both appearance and dynamics of input processes.

7. The method of claim 1 wherein the the method steps of claim 1 are configured as instructions disposed on a non-transitory computer readable medium.

8. The method of claim 1 further comprising receiving datasets from an imaging machine.

9. The method of claim 1 further comprising outputting the heatmap to a graphical user interface.

10. A system for integrating datasets and other factors comprising:
 a source of datasets;
 a processing device configured with processor executable instructions to perform operation comprising:
  receiving clinical data input in the form of the datasets, wherein the datasets are from various input sources, and wherein the datasets include computer-based medical image data, such as from magnetic resonance imaging or positron emission tomography;
  mapping each of a number of input parameters to a point in an informatics embedded space using a machine learning informatics model in combination with a distance metric or correlation coefficient to provide a unified description to capture both appearance and dynamics of the input, wherein the clinical data input is a number of input parameters;
  detecting complex interactions from input sources or domains within the informatics embedded space, using the processing device, wherein the processor implements advanced unsupervised machine learning combined with statistical methods to detect the complex interactions;
  outputting quantitative information with a pairwise correlation of points in the informatics embedded space that are representative of a group of points;
  generating a heatmap representative of the correlation of the points to determine relationships and patterns to enable detection and contribution of each data parameter to the embedded space;
  outputting the heatmap to a user as a visualization using a graphical user interface, wherein the heatmap is usable for diagnosis and treatment response.

11. The system of claim 10 further comprising the space taking the form of a two-dimensional space.

12. The system of claim 10 further comprising the space taking the form of a three-dimensional space.

13. The system of claim 10 further comprising making medical diagnosis.

14. The system of claim 13 further comprising assessing cancer.

15. The system of claim 10 further comprising embedded space taking the form of a unified description capturing both appearance and dynamics of input processes.

16. The system of claim 10 further comprising a computing device.

17. The system of claim 10 further comprising receiving datasets from an imaging machine.

18. The system of claim 10 further comprising outputting the heatmap to a graphical user interface.

* * * * *